(12) United States Patent
Stefanov

(10) Patent No.: US 11,504,477 B2
(45) Date of Patent: Nov. 22, 2022

(54) DUAL-CHAMBER DELIVERY DEVICE

(71) Applicant: SHL MEDICAL AG, Zug (CH)

(72) Inventor: Slobodan Stefanov, Deerfield Beach, FL (US)

(73) Assignee: SHL MEDICAL AG, Zug (CH)

( * ) Notice: Subject to any disclaimer, the term of this patent is extended or adjusted under 35 U.S.C. 154(b) by 608 days.

(21) Appl. No.: 16/337,678

(22) PCT Filed: Oct. 2, 2017

(86) PCT No.: PCT/EP2017/074989
§ 371 (c)(1),
(2) Date: Mar. 28, 2019

(87) PCT Pub. No.: WO2018/065368
PCT Pub. Date: Apr. 12, 2018

(65) Prior Publication Data
US 2020/0023132 A1 Jan. 23, 2020

Related U.S. Application Data

(60) Provisional application No. 62/404,868, filed on Oct. 6, 2016.

(51) Int. Cl.
*A61M 5/24* (2006.01)
*A61M 5/19* (2006.01)
(Continued)

(52) U.S. Cl.
CPC ............ *A61M 5/2448* (2013.01); *A61M 5/19* (2013.01); *A61M 5/2422* (2013.01);
(Continued)

(58) Field of Classification Search
CPC ............ A61M 2005/1787; A61M 5/19; A61M 5/2422; A61M 5/2448; A61M 5/2455;
(Continued)

(56) References Cited

U.S. PATENT DOCUMENTS 4,099,520 A    7/1978  Decker et al.
4,394,863 A *  7/1983  Bartner .............. A61M 5/2066
                                                    604/157

(Continued)

FOREIGN PATENT DOCUMENTS

JP    S62502874 A    11/1987
JP    2004525379 A    8/2004
(Continued)

OTHER PUBLICATIONS

International Search Report and Written Opinion for Int. App. No. PCT/EP2017/074989, dated Feb. 5, 2018.

*Primary Examiner* — Shefali D Patel
(74) *Attorney, Agent, or Firm* — McDonnell Boehnen Hulbert & Berghoff LLP

(57) ABSTRACT

A drug delivery device configured to provide a dose of a first medicament followed by a dose of a second medicament is disclosed. The device includes a main exterior body and an interior body. The device further includes a dual-chamber reservoir with (i) a first chamber holding the first medicament and (ii) a second chamber holding the second medicament. The device also includes a needle and a plunger. After activation of the device, the plunger is configured to (i) move the dual-chamber reservoir a given distance in a distal direction with respect to the interior body so that a distal end of the needle extends out of the interior body and (ii) after moving the dual-chamber reservoir the given distance, move in the distal direction with respect to the dual-chamber reservoir so as to eject from the needle the first medicament followed by the second medicament.

13 Claims, 7 Drawing Sheets

(51) Int. Cl.
*A61M 5/315* (2006.01)
*A61M 5/20* (2006.01)
*A61M 5/32* (2006.01)
*A61M 5/178* (2006.01)

(52) U.S. Cl.
CPC ...... *A61M 5/2459* (2013.01); *A61M 5/31596* (2013.01); *A61M 5/2033* (2013.01); *A61M 5/2066* (2013.01); *A61M 5/31505* (2013.01); *A61M 5/31578* (2013.01); *A61M 5/3202* (2013.01); *A61M 5/3294* (2013.01); *A61M 2005/1787* (2013.01); *A61M 2005/206* (2013.01)

(58) Field of Classification Search
CPC ............ A61M 5/2459; A61M 5/31596; A61M 5/2033; A61M 5/2066; A61M 5/31505; A61M 5/31578; A61M 5/3202; A61M 5/3294; A61M 2005/206
See application file for complete search history.

(56) References Cited

U.S. PATENT DOCUMENTS

| | | | |
|---|---|---|---|
| 4,723,937 | A | 2/1988 | Sarnoff et al. |
| 5,279,606 | A | 1/1994 | Haber et al. |
| RE35,986 | E | 12/1998 | Ritson et al. |
| 8,353,877 | B2 * | 1/2013 | Hallahan ............... A61D 1/02 604/191 |
| 2002/0183690 | A1 | 12/2002 | Arnisolle |
| 2009/0182301 | A1 | 7/2009 | Bassarab et al. |
| 2013/0274707 | A1 | 10/2013 | Wilmot et al. |

FOREIGN PATENT DOCUMENTS

| | | |
|---|---|---|
| JP | 2007525247 A | 9/2007 |
| JP | 2013542022 A | 11/2013 |
| WO | 86/06966 A1 | 12/1986 |
| WO | 2012/059450 A1 | 5/2012 |

\* cited by examiner

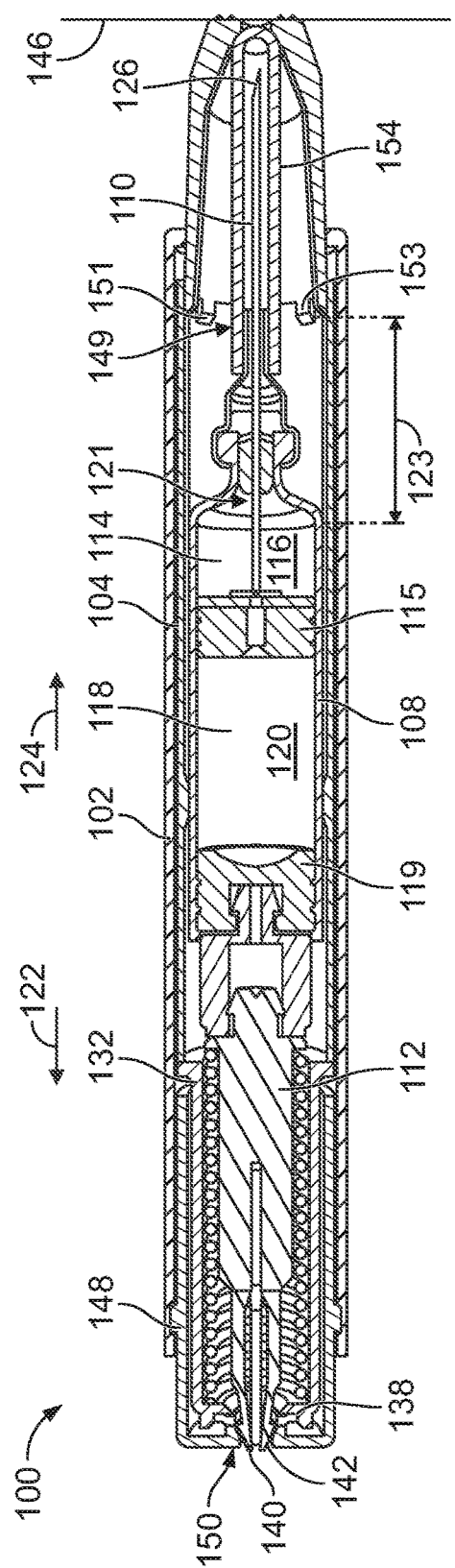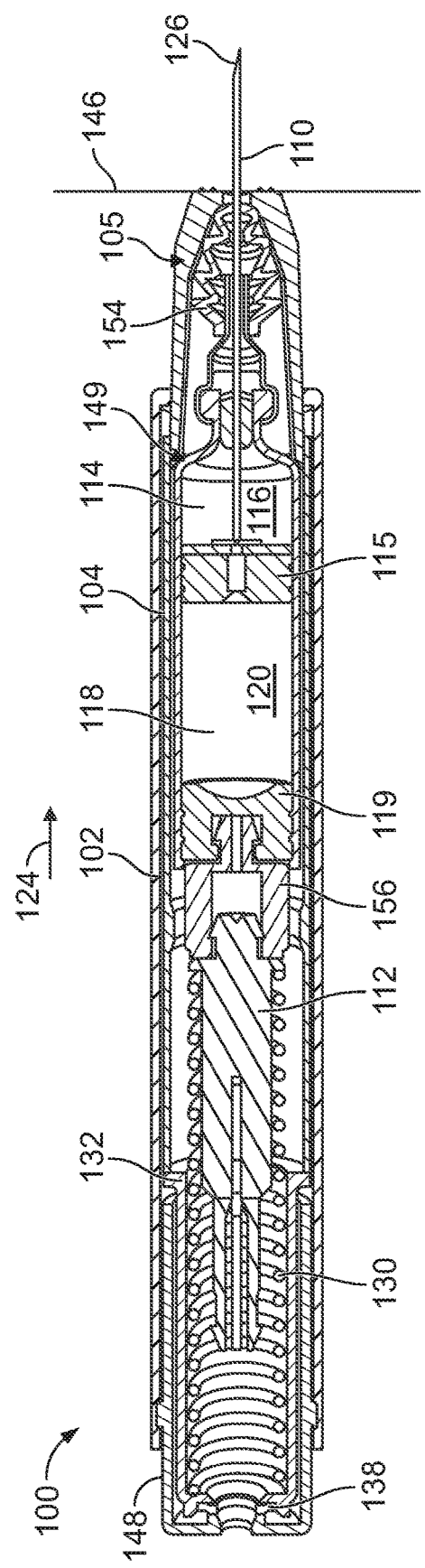

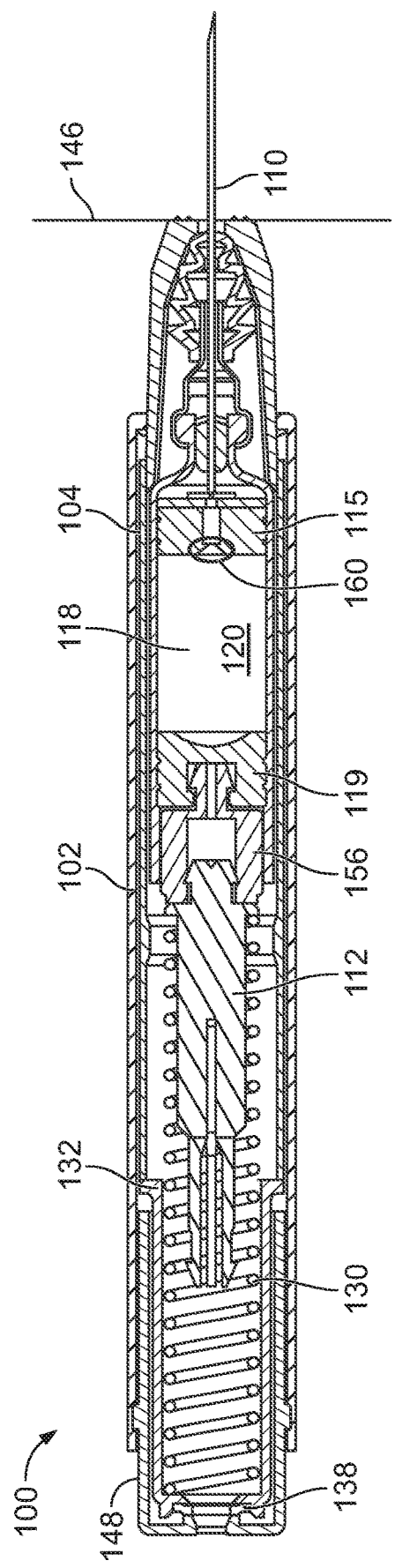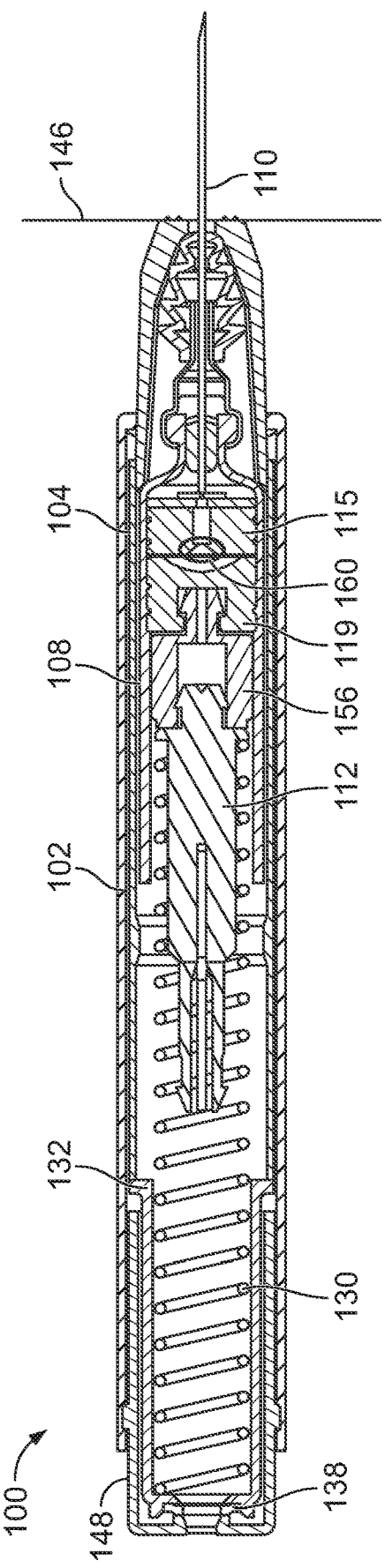
FIG. 8
FIG. 9

DUAL-CHAMBER DELIVERY DEVICE

CROSS REFERENCE TO RELATED APPLICATIONS

The present application is a U.S. National Phase Application pursuant to 35 U.S.C. § 371 of International Application No. PCT/EP2017/074989 filed Oct. 2, 2017, which claims priority to U.S. Provisional Patent Application No. 62/404,868 filed Oct. 6, 2016. The entire disclosure contents of these applications are herewith incorporated by reference into the present application.

TECHNICAL AREA

This present disclosure relates to drug delivery devices such as automatic injection devices.

BACKGROUND

Unless otherwise indicated herein, the materials described in this section are not prior art to the claims in this application and are not admitted to be prior art by inclusion in this section.

In some situations, it is desirable for patients to be able to administer drugs and medicament by themselves, e.g., without the need for trained medical staff to administer the drugs. Further, in some situations, it is desirable to administer a first medicament followed by a second medicament in a single injection. There are a number of different existing delivery devices with varying degrees of automatic functions. For instance, existing automatic injection devices provide a means for automatically propelling a plunger forward to eject medicament from the automatic injection device in response to activation of the device. Further, existing automatic injection devices provide a means for ejecting a dose of a first medicament and a dose of a second medicament.

In existing devices, the means for penetrating an injection site and injecting a dose of a first medicament and a dose of a second medicament are often complex and expensive to manufacture. There is, therefore, a desire to reduce the cost of manufacturing automatic injection devices while maintaining the reliability of the injection device to penetrate an injection site and inject a dose of a first medicament followed by a dose of a second medicament.

SUMMARY

A dual-chamber drug delivery device is provided. In an example embodiment, the drug delivery device includes a main exterior body and an interior body axially moveable with respect to the main exterior body. Further, the drug delivery device includes a dual-chamber reservoir arranged in the interior body and axially moveable with respect to the interior body. The dual-chamber reservoir includes (i) a first chamber holding a first medicament and (ii) a second chamber holding a second medicament. Still further, the drug delivery device includes a plunger and a needle in fluid communication with the dual-chamber reservoir. Axial movement of the interior body in a proximal direction with respect to the main exterior body activates the drug delivery device. Further, after activation of the drug delivery device, the plunger is configured to (i) move the dual-chamber reservoir a given distance in a distal direction with respect to the interior body so that a distal end of the needle extends out of the interior body and (ii) after moving the dual-chamber reservoir the given distance, move in the distal direction with respect to the dual-chamber reservoir so as to eject from the needle the first medicament followed by the second medicament.

In another example embodiment, the drug delivery device includes a main exterior body and an interior body axially moveable in a proximal direction with respect to the main exterior body to activate the drug delivery device. The drug delivery device further includes a dual-chamber reservoir arranged in the interior body and axially moveable with respect to the interior body. The dual-chamber reservoir includes a (i) first stopper slidably arranged in the dual-chamber reservoir and having a ruptureable membrane and (ii) a second stopper slidably arranged in the dual-chamber reservoir. A first chamber holding a first medicament is located between the first stopper and a distal end of the reservoir, and a second chamber holding a second medicament is located between the first stopper and the second stopper. Still further, the drug delivery device includes a needle in fluid communication with the first chamber and axially fixed to the first stopper. Axial movement of the interior body in a proximal direction with respect to the main exterior body activates the drug delivery device. Further, after activation of the drug delivery device, the plunger is configured to (i) move the dual-chamber reservoir a given distance in a distal direction with respect to the interior body so that a distal end of the needle extends out of the interior body and (ii) after moving the dual-chamber reservoir the given distance, move in the distal direction with respect to the dual-chamber reservoir so as to (a) eject from the needle substantially all of the first medicament, (b) subsequently rupture the ruptureable membrane to establish fluid communication between the needle and the second chamber, and (c) subsequently eject from the needle substantially all of the second medicament.

In yet another example embodiment, the drug delivery device includes a main exterior body and an interior body axially moveable in a proximal direction with respect to the main exterior body to activate the drug delivery device. The drug delivery device further includes a dual-chamber reservoir arranged in the interior body and axially moveable with respect to the interior body. The dual-chamber reservoir includes: (i) a first stopper slidably arranged in the dual-chamber reservoir; (ii) a second stopper slidably arranged in the dual-chamber reservoir, wherein a first chamber holding a first medicament is located between the first stopper and a distal end of the reservoir, wherein a second chamber holding a second medicament is located between the first stopper and the second stopper; and (iii) a conduit disposed in the first chamber, wherein the conduit comprises at least one conduit needle configured to establish fluid communication with the second chamber during an injection process. Still further, the drug delivery device includes a needle in fluid communication with the first chamber and axially fixed to the first stopper. Axial movement of the interior body in a proximal direction with respect to the main exterior body activates the drug delivery device. Further, after activation of the drug delivery device, the plunger is configured to (i) move the dual-chamber reservoir a given distance in a distal direction with respect to the interior body so that a distal end of the needle extends out of the interior body and (ii) after moving the dual-chamber reservoir the given distance, move in the distal direction with respect to the dual-chamber reservoir so as to (a) eject from the needle substantially all of the first medicament, (b) subsequently force the at least one conduit needle to fully penetrate the first stopper and establish fluid communication with the second chamber, and (c) subsequently eject from the needle substantially all of the second medicament.

In still yet another example embodiment, a method in a dual-chamber drug delivery device is provided. The dual-chamber drug delivery device includes (i) a body, (ii) a dual-chamber reservoir, (iii) a first stopper slidably arranged in the dual-chamber reservoir, (iv) a second stopper slidably arranged in the dual-chamber reservoir, wherein a first chamber holding a first medicament is between the first stopper and a distal end of the reservoir, and wherein a second chamber holding a second medicament is between the first stopper and the second stopper, (v) a needle in fluid communication with the dual-chamber reservoir, and (vi) a plunger. The method includes, in response to activation of the drug delivery device, the plunger moving the dual-chamber reservoir through the body of the device to force the needle out of the body and to penetrate an injection site. The method further includes, after moving the dual-chamber reservoir through the body of the device to expose the needle and penetrate an injection site, the plunger moving through the dual-chamber reservoir to force out of the drug delivery device substantially all the first medicament from the first chamber followed by substantially all of the second medicament from the second chamber.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE DRAWINGS

Exemplary embodiments are described herein with reference to the drawings, in which:

FIG. 4 illustrates a cross-sectional view of the drug delivery device of FIG. 1 prior to needle penetration and medicament injection, according to an example embodiment of the present disclosure.

FIG. 5 illustrates a cross-sectional view of the drug delivery device of FIG. 1 after needle penetration and prior to medicament injection, according to an example embodiment of the present disclosure.

FIG. 8 illustrates a cross-sectional view of the drug delivery device of FIG. 1 after substantially all of a first medicament has been ejected from the drug delivery device, according to an example embodiment of the present disclosure.

FIG. 9 illustrates a cross-sectional view of the drug delivery device of FIG. 1 after substantially all of a second medicament has been ejected from the drug delivery device, according to an example embodiment of the present disclosure.

DETAILED DESCRIPTION

Figure 1:
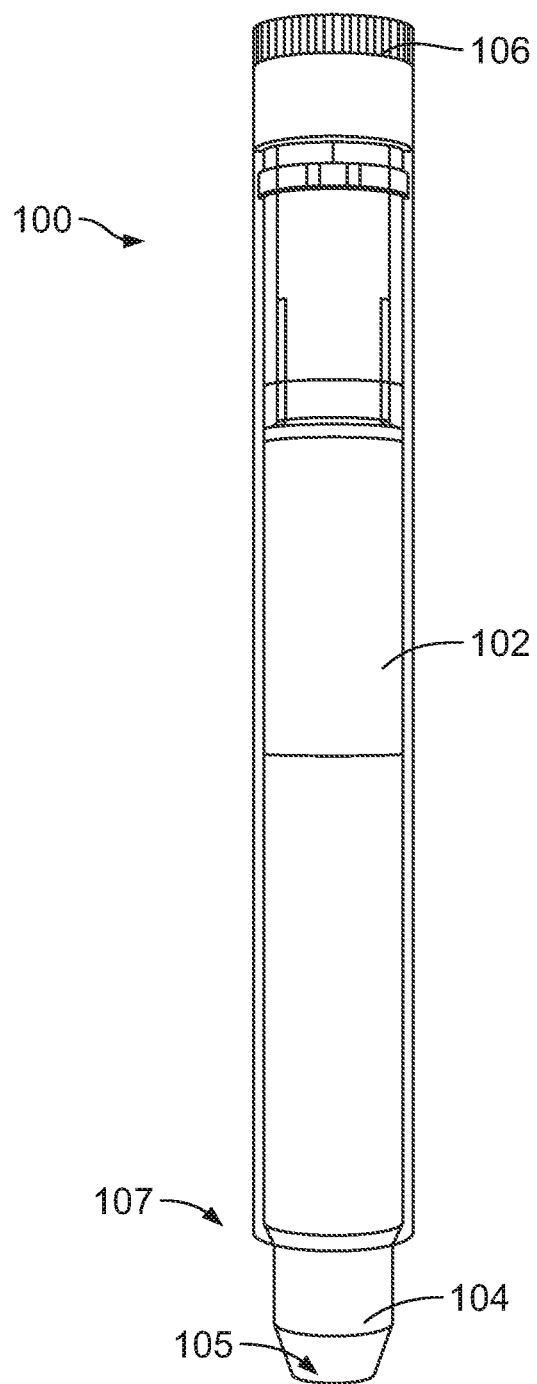
FIG. 1 illustrates a perspective view of an example drug delivery device having an example dual-chamber reservoir, according to an example embodiment of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The methods and systems in accordance with the present disclosure beneficially provide improved methods and systems for automatically ejecting a first and second medicament from an automatic injection device. The disclosed methods and systems provide a reliable, intuitive, and user-friendly drug delivery device that includes improved means for automatically propelling a plunger forward for needle penetration and injecting two medicaments one after the other. Further, the disclosed methods and systems provide cost effective means for needle penetration and injecting two medicaments one after the other and thus help to reduce the cost of manufacturing automatic injection devices.

In accordance with an example embodiment of the present disclosure, a drug delivery device includes a main exterior body and an interior body axially moveable with respect to the main exterior body. The drug delivery device further includes a dual-chamber reservoir arranged in the interior body and axially moveable with respect to the interior body. The dual-chamber reservoir includes (i) a first chamber holding a first medicament and (ii) a second chamber holding a second medicament. Still further, the drug delivery device includes a plunger, as well as a needle in fluid communication with the dual-chamber reservoir. The drug delivery device is configured such that axial movement of the interior body in a proximal direction with respect to the main exterior body activates the drug delivery device. Further, after activation of the drug delivery device, the plunger is configured to move the dual-chamber reservoir a given distance in a proximal direction with respect to the interior body so that a proximal end of the needle extends out of the interior body. Still further, the plunger is configured to, after moving the dual-chamber reservoir the given distance, move in the proximal direction with respect to the dual-chamber reservoir so as to eject from the needle the first medicament followed by the second medicament.

FIG. 1 generally illustrates an example drug delivery device that includes a dual-chamber sequential injection mechanism that allows it to inject two medicaments one after the other. In particular, FIG. 1 illustrates a drug delivery device 100 in an initial state prior to injection. Drug delivery device 100 includes a main exterior body 102 and interior body 104. Interior body 104 is axially moveable with respect to main exterior body 102. Exterior body 102 surrounds the majority of the interior body 104; however, a proximal end 105 of the interior body 104 extends beyond a proximal end 107 of the main exterior body 102. In the example of FIG. 1, drug delivery device 100 also includes safety cap 106.

With reference to FIG. 4, drug delivery device 100 also includes a dual-chamber reservoir 108, a needle 110 in fluid communication with the dual-chamber reservoir 108, and a plunger 112. The dual-chamber reservoir 108 is arranged in the interior body 104 and is axially moveable with respect to the interior body 104. Further, the dual-chamber reservoir 108 includes (i) a first chamber 114 holding a first medicament 116 and (ii) a second chamber 118 holding a second medicament 120. Drug delivery device 100 also includes a first stopper 115 slidably arranged in the dual-chamber reservoir 108 and a second stopper 119 slidably arranged in the dual-chamber reservoir 108. First stopper 115 and second stopper 119 are in sliding fluid-tight engagement with the inner walls of dual-chamber reservoir 108. The first chamber 114 is between the first stopper 115 and a proximal end 121 of the reservoir, and the second chamber 118 is between the first stopper 115 and the second stopper 119.

As will be explained in greater detail below, axial movement of the interior body 104 in a distal direction 122 with respect to the main exterior body 102 activates the drug delivery device 100. Further, after activation of the drug delivery device 100, the plunger 112 is configured to (i) move the dual-chamber reservoir 108 a given distance 123 in a proximal direction 124 with respect to the interior body 104 so that a proximal end 126 of the needle 110 extends out of the interior body 104 and (ii) after moving the dual-chamber reservoir 108 the given distance 123, move in the proximal direction 124 with respect to the dual-chamber reservoir 108 so as to eject from the needle 110 the first medicament 116 followed by the second medicament 120. When plunger 112 moves in the proximal direction 124 with respect to the dual-chamber reservoir 108, the plunger 112 will move axially through the reservoir 108 so as to push the stoppers 115, 119 for medicament injection.

In the example embodiment of FIGS. 1-9, dual-chamber reservoir 108 is a dual-chamber syringe. However, any suitable type of medicament reservoir may be used in the disclosed drug delivery device 100, such as a syringe, an ampoule, a cartridge, an enclosure, etc. Further, the first medicament 116 and the second medicament 120 may be any suitable substances used for medical treatment. In an example embodiment, the first medicament is different than the second medicament. In another example embodiment, the first and second medicaments are both prescription drugs. Other medicaments are possible as well.

Operation of drug delivery device 100 is described in greater detail with reference to FIGS. 2-9. In particular, an example safety-cap mechanism is described with reference to FIGS. 2-3. Further, activation of the drug delivery device 100 is described with reference to FIG. 4 and needle penetration is described with reference to FIG. 5. Still further, medicament injection is described with reference to FIGS. 7-9.

Figure 2:
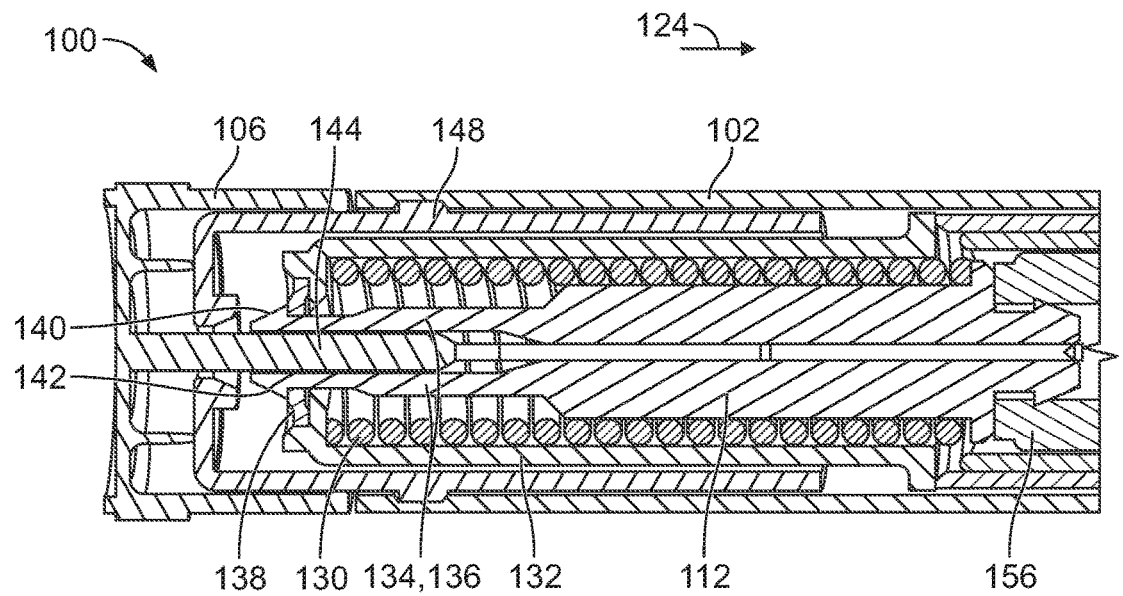
FIG. 2 illustrates a partial cross-sectional view of the drug delivery device of FIG. 1 prior to removal of an example safety cap, according to an example embodiment of the present disclosure.

FIG. 2 illustrates a partial cross-sectional view of the drug delivery device 100 prior to removal of safety cap 106. As shown in FIG. 2, drug delivery device 100 includes a biasing member 130. Biasing member 130 is configured to bias the plunger 112 in proximal direction 124. Prior to activation of drug delivery device 100, the biasing member 130 is in a compressed state and continuously pushes against the plunger 112 as well as the inner surface of interior retainer 132. At the same time, plunger arms 134, 136 are held by a retaining washer 138, which is disposed at a distal end of interior retainer 132. As a result, the plunger 112 is prevented from moving axially away from the safety cap 106. In particular, distal end portions 140, 142 of plunger arms 134, 136 are held by the retaining washer 138. Further, before the safety cap 106 is removed, a safety pin 144 of safety cap 106 is located between the plunger arms 134, 136 and thus prevents the plunger arms 134, 136 from closing and escaping from the retaining washer 138.

In this example embodiment shown in FIG. 2, plunger 112 includes two plunger arms 134, 136. However, in other example embodiments, more or fewer plunger arms are possible. Further, in the example embodiment shown in FIG. 2, biasing member 130 is a spring. However, other biasing members are possible as well. For instance, in another example embodiment, the biasing member is a pneumatic-based biasing member such as a pressurized gas source.

Figure 3:
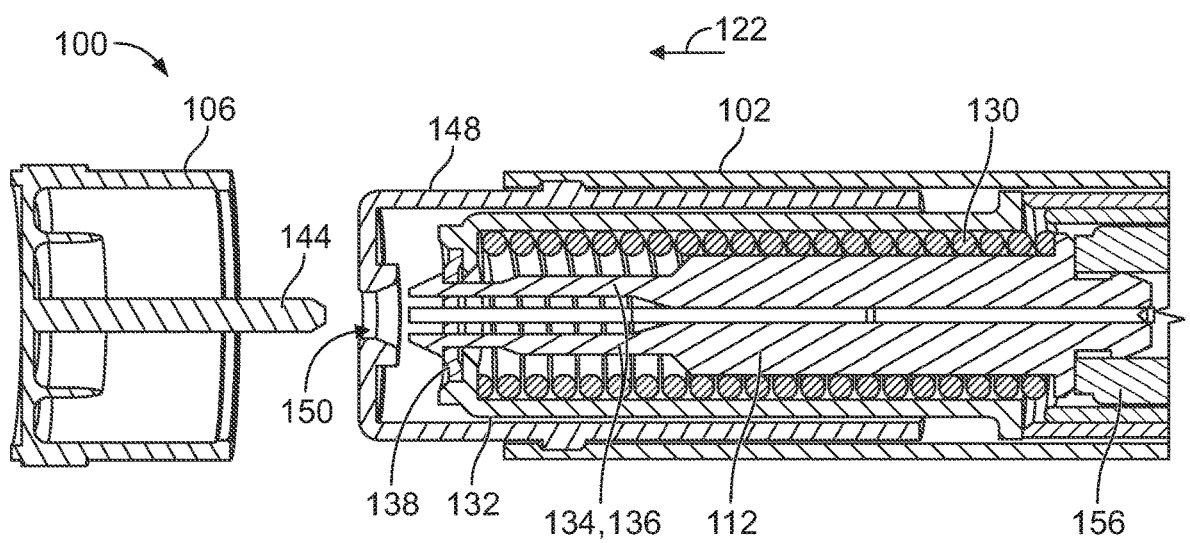
FIG. 3 illustrates a partial cross-sectional view of the drug delivery device of FIG. 1 after removal of the example safety cap of FIG. 2, according to an example embodiment of the present disclosure.

FIG. 3 illustrates a partial cross-sectional view of the drug delivery device 100 after removal of safety cap 106. As seen in FIG. 3, the safety cap 106 may be moved in distal direction 122 relative to the main exterior body 102, so as to be removed from the drug delivery device 100. After removal, the safety pin 144 of safety cap 106 is no longer located between the plunger arms 134, 136. Thus, the plunger arms 134, 136 can later be closed together during the activation process so as to be narrow enough for escaping from the retaining washer 138.

FIG. 4 illustrates a cross-sectional view of drug delivery device 100 during the activation process and prior to trigger needle penetration and medicament injection. As mentioned above, axial movement of the interior body 104 in a distal direction 122 with respect to the main exterior body 102 activates the drug delivery device 100. This activation may occur when a user presses the drug delivery device 100 against an injection site, such as injection site 146. The pressing force pushes the interior body 104 against the interior retainer 132 which in turns brings the interior body 104, retaining washer 138, and the attached plunger 112 toward the exterior retainer 148. Such movement of the interior body 104, retaining washer 138, and the attached plunger 112 toward the exterior retainer 148 can be seen by comparing FIG. 3 with FIG. 4.

When the end portions 140, 142 of plunger arms 134, 136 reach the opening 150 of exterior retainer 148, the opening 150 forces the end portions 140, 142 as well as the whole plunger arms 134, 136 to bend inward and have a diameter smaller than that of the opening on the retaining washer 138. The biasing member 130 can then release stored energy, so as to push the plunger 112 away from the retaining washer 138 and exterior retainer 148. In particular, biasing member 130 extends distally and starts pushing the plunger 112 in proximal direction 124.

As mentioned above, after activation of the drug delivery device 100, the plunger 112 is configured to move the dual-chamber reservoir 108 a given distance 123 in a proximal direction 124 with respect to the interior body 104 so that a proximal end 126 of the needle 110 extends out of the interior body 104. This action causes the needle 110 to penetrate the injection site 146 to a desired depth. The plunger 112 is also configured to, after moving the dual-chamber reservoir 108 the given distance 123, move in the proximal direction 124 with respect to the dual-chamber reservoir 108 so as to eject from the needle 110 the first medicament 116 followed by the second medicament 120. This injection operation of (i) needle penetration to a desired depth followed by (ii) medicament delivery is described further with respect to FIGS. 5-9.

FIG. 5 illustrates a cross-sectional view of drug delivery device 100 after needle penetration and prior to medicament injection. As seen in FIG. 5, the plunger 112 has been released from the retaining washer 138 and is pushed by biasing member 130 in proximal direction 124. Initially, when the plunger 112 is released, the biasing member 130 starts to push both the plunger 112 as well as the dual-chamber reservoir 108 toward the proximal end 105 of interior body 104. The dual-chamber reservoir 108 travels the given distance 123 relative to the inner body 104 such that needle penetration into injection site 146 takes place.

Interior body 104 includes a stop feature that limits travel of the dual-chamber reservoir 108 in distal direction 108. For instance, interior body 104 includes a reduced diameter portion 149 that acts as the stop feature and limits the proximal travel of the dual-chamber reservoir 108. The reduced diameter portion 149 may include one or more protrusions, such as protrusions 151 and 153 (see FIG. 4). In an example embodiment, the force required to move the dual-chamber reservoir 108 through the interior body 104 to the stop feature is less than the force required to move the second stopper 119 through the dual-chamber reservoir 108. Thus, the dual-chamber reservoir 108 will move proximally through the interior body 104 to the stop feature prior second stopper 119 moving through the dual-chamber reservoir 108. This will ensure that that needle 110 will be extended a desired amount prior to the ejection of any medicament through the needle 110.

Returning to FIG. 5, drug delivery device 100 includes a collapsible needle cover 154 covering the needle 110. The collapsible needle cover 154 is configured to collapse and be penetrated by the needle 110 when the plunger 112 moves the dual-chamber reservoir 108 the given distance 123. During this movement, the needle cover 154 is squashed as cover 154 is pushed against the interior body 104, and then the needle 110 penetrates both the needle cover 154 and injection site 146.

Figure 6:
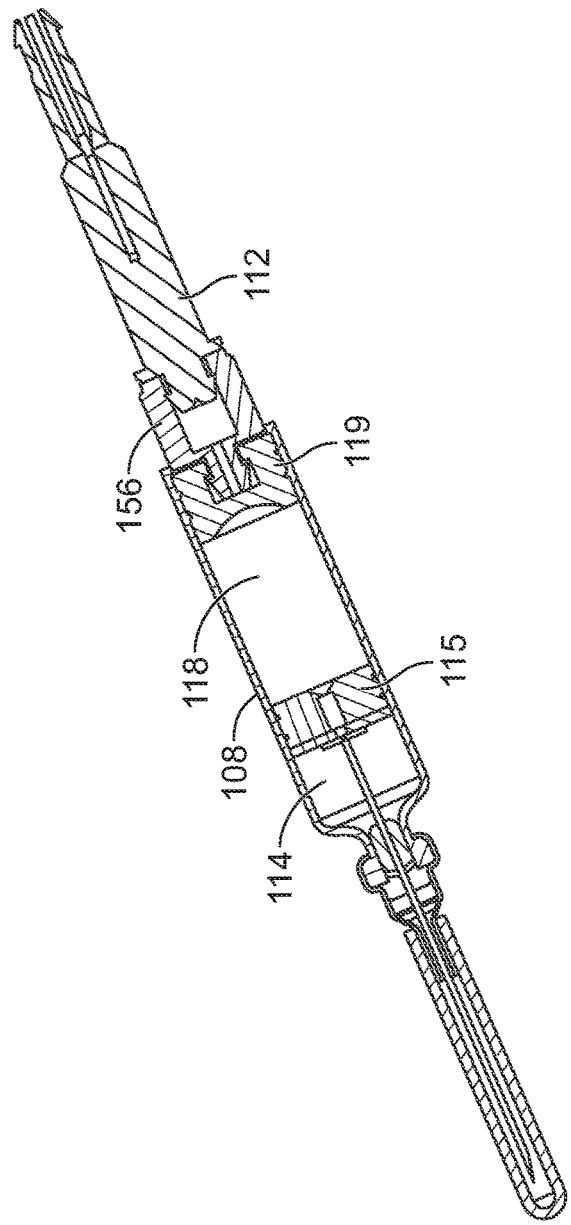
FIG. 6 illustrates a cross-sectional view of example components of the drug delivery device of FIG. 1, according to an example embodiment of the present disclosure.

In an example embodiment, drug delivery device 100 includes a stopper grabber 156 that evenly distributes the force from the plunger 112 to the second stopper 119 during medicament injection. FIG. 6 illustrates the assembly of plunger 112, stopper grabber 156, and stoppers 115, 119, which are all moved by biasing member 130 for medicament injection. In an example embodiment, the stopper grabber 156 includes several ribs (not shown) to be in contact with the inner surface of the inner walls of the dual-chamber reservoir 108 in order to maintain axial location of the assembly during medicament injection, by evenly distributing the force from the biasing member 130 and plunger 112 to the second stopper 119. In another example embodiment, the plunger 112 acts directly on second stopper 119 rather than through a stopper grabber 156.

Figure 7:
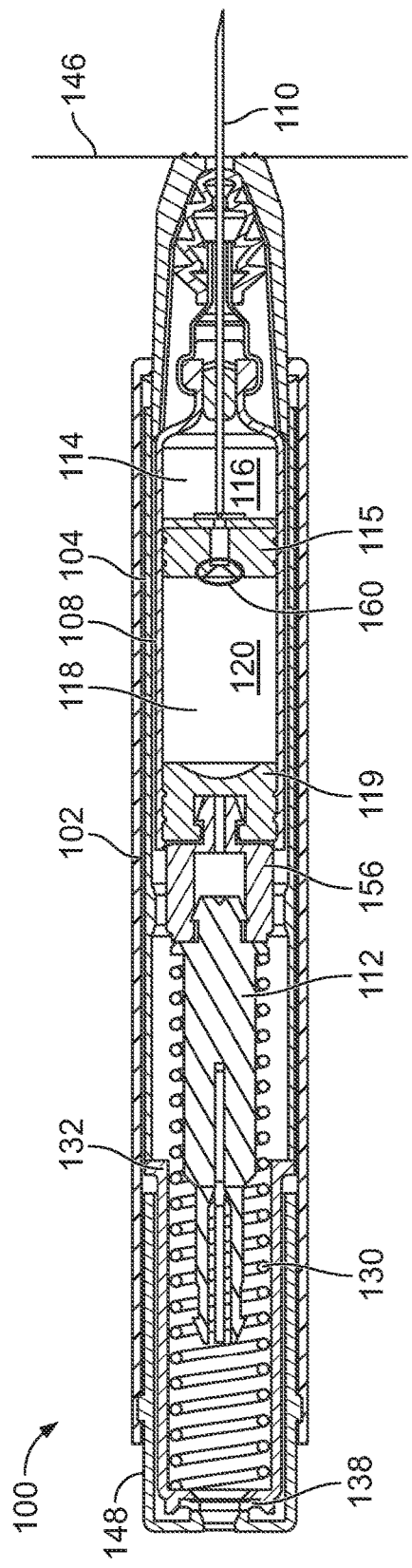
FIG. 7 illustrates a cross-sectional view of the drug delivery device of FIG. 1 after the plunger is released for medicament injection, according to an example embodiment of the present disclosure.

FIG. 7 illustrates a cross-sectional view of the drug delivery device 100 after the plunger 112 is released from the retainers 132, 148 and driven by the biasing member 130 to apply force on the stopper grabber 156. After the needle penetration takes place, the biasing member 130 continuously pushes the plunger 112, stopper grabber 156, and second stopper 119 through the dual-chamber reservoir 108 toward the needle 110 in order to force the medicament out of the needle and into the injection site. In particular, after the plunger 112 moves the dual-chamber reservoir 108 the given distance 123 for needle penetration, (i) force from the plunger 112 is transferred to the second stopper 119, (ii) the second stopper 119 pushes the second medicament 120 in the second chamber 118, (iii) the second medicament 120 consequently pushes the first stopper 115, and (iv) the first stopper 115 consequently pushes the first medicament 116 in the first chamber 114 out of the needle 110.

In an example embodiment, the needle 110 is axially fixed to the first stopper 115. Therefore, as first stopper 115 moves axially through the dual-chamber reservoir 108 to eject to the first medicament 116, the needle 110 further penetrates the injection site (see FIG. 7 compared to FIG. 8). In another example embodiment, rather than being axially fixed to the first stopper, the needle 110 is axially fixed to a distal end of the dual-chamber reservoir 108.

As seen in FIG. 7, drug delivery device 100 includes a ruptureable membrane 160 separating the first chamber 114 from the second chamber 118. The ruptureable membrane 160 is configured to rupture due to a pressure imbalance between the first chamber 114 and the second chamber 118 that occurs when substantially all the first medicament 116 in the first chamber 114 is ejected. During the injection of the first medicament 116, the stopper grabber 156 transfers force to the second stopper 119 which in turn pushes the medicament 120 in the second chamber 118, which in turns pushes the first stopper 115 and then the medicament 116 in the first chamber 114 out of the needle 110 and into the injection site 146. At this stage of ejecting the first medicament 116, there are medicaments 116, 120 in both chambers which maintain a pressure balance between both chambers 114, 118. Thus, the membrane 160 can continue separating the two chambers from one another without rupture.

However, subsequent to ejecting all or substantially all of the first medicament 116, the ruptureable membrane 160 ruptures to establish fluid communication between the needle 110 and the second chamber 118. FIG. 8 illustrates drug delivery device 100 after substantially all of a first medicament 116 has been ejected from the drug delivery device 100 into the injection site 146 in full. At this stage, there is now a pressure imbalance between the first chamber 114 and the second chamber 118. The second medicament 120 in the second chamber 118, under forces from the biasing member 130, continues pushing and eventually ruptures the membrane 160 shortly after the first chamber 114 is emptied or substantially emptied.

After this rupture, the second medicament 120 is then ejected from the drug delivery device 100. In particular, after the membrane 160 ruptures, the second medicament 120 can flow into the first chamber 114. The second medicament 120 previously in the second chamber 118 is then pushed by the biasing member 130 and exits the dual-chamber reservoir 108 through the needle 110 in the first chamber 114 and into the injection site 146. FIG. 9 illustrates a drug delivery device 100 after substantially all of the second medicament 120 has been ejected.

In an example embodiment, the first stopper 115 comprises the ruptureable membrane 160. For instance, the first stopper 115 may be manufactured (e.g., via injection molding) to include the ruptureable membrane 160. In another example embodiment, the membrane 160 is attached to the first stopper 115 in any suitable fashion. For example, the membrane 160 may be attached to the first stopper 115 with an adhesive.

In an example embodiment, during dose delivery, the user can hear and/or feel an audible and/or tactile feedback (e.g., clicking) throughout the dose delivery. For instance, the drug delivery device 100 may include a clicker that produces a clicking sound when the plunger 112 is being propelled forward in the proximal direction 124. The end of injection may be indicated by the audible/tactile clicking having stopped. Additionally or alternatively, the drug delivery device 100 may include a window that allows a user to see when injection is complete. In such an example where the drug delivery device 100 includes the window, the end of delivery is indicated by the second stopper 119 and plunger 112 having stopped moving. Other indications of dose delivery being complete are possible as well.

Figure 10:
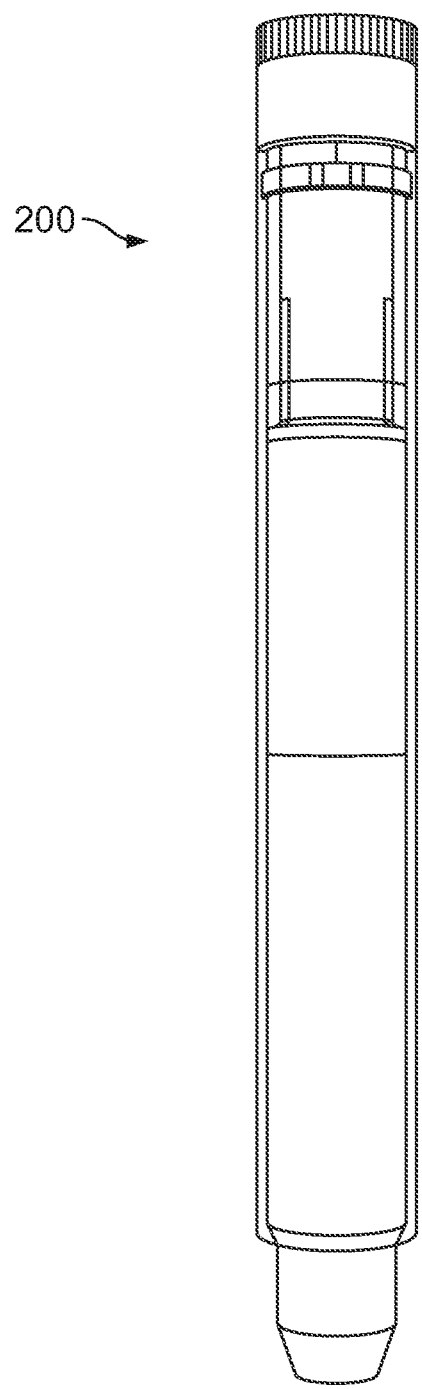
FIG. 10 illustrates a perspective view of an example drug delivery device having an example dual-chamber reservoir, according to an example embodiment of the present disclosure.
Figure 11:
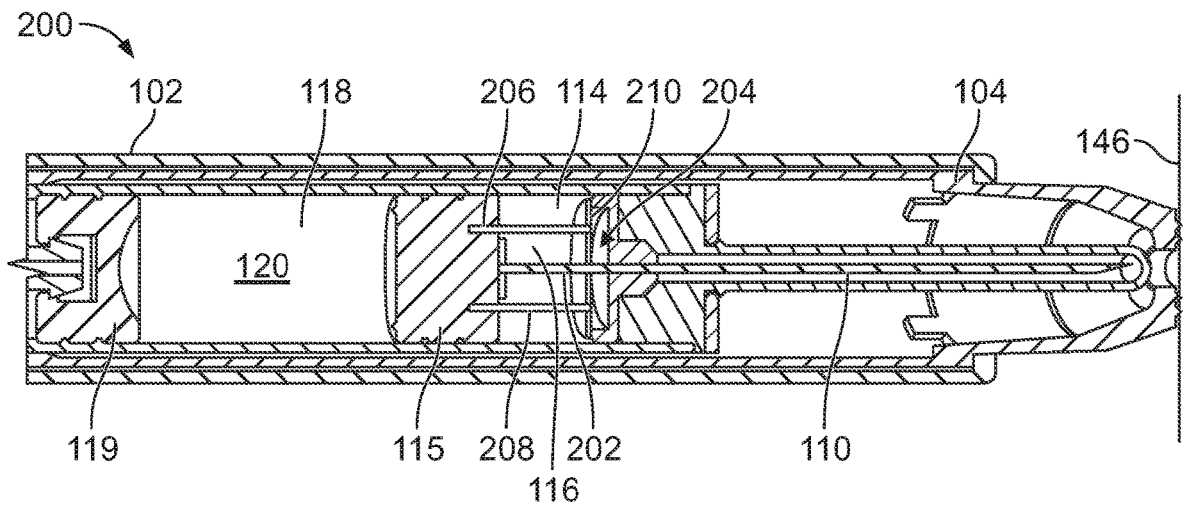
FIG. 11 illustrates a partial cross-sectional view of the drug delivery device of FIG. 10, according to an example embodiment of the present disclosure.

FIGS. 10 and 11 depict another example embodiment of the disclosed dual-chamber drug delivery device. In particular, FIGS. 10 and 11 depict drug delivery device 200. The drug delivery device 200 operates in a similar fashion as drug delivery devices 100; however, rather than including ruptureable membrane 160, drug delivery device 200 includes a conduit disposed in the first chamber 114. The conduit is configured to establish fluid communication with the second chamber 118 during the injection process. Further, the conduit comprises at least one conduit needle configured to penetrate the first stopper 115 and establish the fluid communication with the second chamber 118. Other elements of drug delivery device 200 may be the same or substantially similar to the other elements drug delivery device 100, and thus drug delivery device 200 is not described in as great of detail. It should be explicitly noted, however, that any possibilities and permutations described above with respect to drug delivery device 100 may equally apply to drug delivery device 200, and vice versa. Further, throughout the description of FIGS. 10-11, elements in drug delivery device 200 that are the same as or substantially similar to elements in drug delivery device 100 are described with like reference numerals.

Turning to FIG. 11, the needle 110 has a needle opening 202 that allows medicament to enter the needle 110 and then to be injected into the injection site 146. On the other hand, the conduit 204 in the first chamber 114 includes two conduit needles 206, 208, with internal passages, that will penetrate the first stopper 115 when it is pushed by the medicament 120 in the second chamber 118 toward the first chamber 114. Although two conduit needles 206, 208 are shown, in other example embodiments, more or fewer conduit needles are possible.

During medicament injection, when the first stopper 115 pushes all or substantially all of the first medicament 116 in the first chamber 114 out through the needle 110, the conduit needles 206, 208 of conduit 204 will penetrate the first stopper 115 and enter the second chamber 118 to form a passage between the two chambers 114, 118. In this way, the medicament 120 in the second chamber 118 can then be pushed by the second stopper 119 (which is pushed by the stopper grabber 156, plunger 112, and biasing member 130). The second medicament 120 then enters the first chamber 114, enters the needle 110 through the needle opening 202, and thereafter exits the needle 110.

In an example embodiment, the conduit needles 206, 208 are sized such that the needles 206, 208 fully penetrate the first stopper 115 and establish the fluid communication with the second chamber 118 subsequent to all or substantially all of a first medicament 116 in the first chamber 114 being ejected. After the needles 206, 208 fully penetrate the first stopper 115, needle opening 202 will be located in a proximal portion 210 of the first chamber 114. The second medicament 120 will flow through conduit needles 206, 208 to the distal portion 210 of the first chamber 114 and then through the needle opening 202, so as to be ejected from needle 110.

Figure 12:
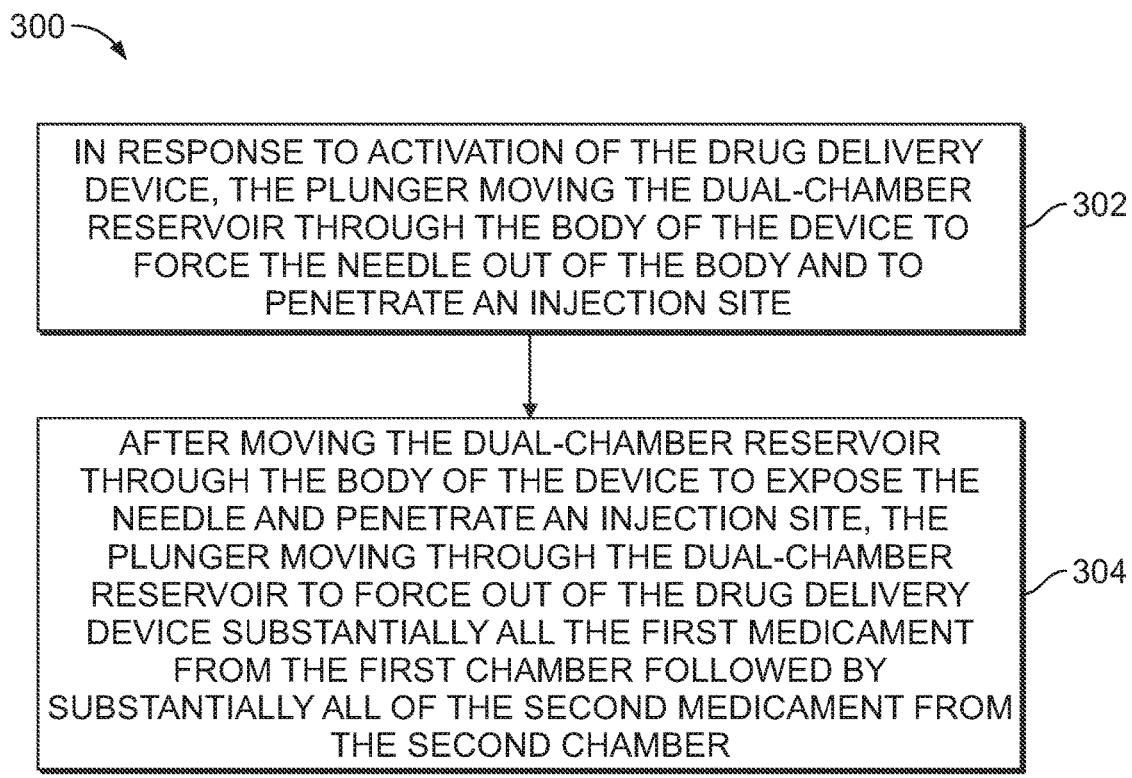
FIG. 12 illustrates an example method, according to an example embodiment of the present disclosure.

FIG. 12 illustrates an example method 300 that can be carried out in a dual-chamber drug delivery device in accordance with the present disclosure, such as drug delivery device 100 or 200. The method includes, at block 302, in response to activation of the drug delivery device, the plunger moving the dual-chamber reservoir through the body of the device to force the needle out of the body and to penetrate an injection site. The method further includes, at block 304, after moving the dual-chamber reservoir through the body of the device to expose the needle and penetrate an injection site, the plunger moving through the dual-chamber reservoir to force out of the drug delivery device substantially all the first medicament from the first chamber followed by substantially all of the second medicament from the second chamber.

In an example embodiment of method 300, the plunger moving through the dual-chamber reservoir to force out of the drug delivery device substantially all the first medicament followed by substantially all of the second medicament involves: (i) force from the plunger transferring to the second stopper; (ii) the second stopper pushing the second medicament in the second chamber, (iii) the second medicament pushing the first stopper; (iv) the first stopper pushing the first medicament in the first chamber out of the needle; and (v) after the first stopper pushing the first medicament in the first chamber out of the needle, the second stopper pushing the second medicament in the second chamber out of the needle.

In an example embodiment of method 300, the body of the drug delivery device is an interior body, such as interior body 104. In another example of method 300, however, the body of the drug delivery device is a main exterior body of the drug delivery device.

In the examples shown in the Figures, drug delivery devices 100 and 200 are activated by being pressed against injection site 146 after removal of the safety cap 106. However, in other example embodiments, the disclosed drug delivery device may be activated in other ways. In general, the drug delivery device may be activated in any suitable fashion. For instance, in an example embodiment, the drug delivery device includes a push button and the drug delivery device is activated by a combination of the drug delivery device being pressed against an injection site and the push button being depressed by a user. In another example embodiment, the drug delivery device is activated by a push button being depressed by a user. Other types of activation are possible as well.

Further, in the examples shown in the Figures, the exterior retainer 148 is axially fixed to main exterior body 102. In an example embodiment, these elements are manufactured separately and then axially fixed during an assembly of the drug delivery device. However, in another example, these elements may be of unitary construction. Similarly, in the examples shown in the Figures, interior retainer 132 and interior body 104 are manufactured separately and then assembled in the drug delivery device 100. However, in another example, these elements may be of unitary construction.

In the Figures, various engagement features for are shown for providing an engagement between one or more components of the drug delivery device. The engagement features may be any suitable connecting mechanism such as a snap lock, a snap fit, form fit, a bayonet, lure lock, threads or combination of these designs. Other designs are possible as well.

Throughout the description, by the term "substantially" it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide. For instance, in an example embodiment, substantially all of the medicament being ejected from a chamber means at least 95% of the medicament originally held in the chamber is ejected from the chamber. In another example embodiment, substantially all of the medicament being ejected from a chamber means at least 90% of the medicament originally held in the chamber is ejected from the chamber.

Beneficially, the disclosed dual-chamber drug delivery device and disclosed method provide a cost effective means for propelling a plunger forward to penetrate an injection site and eject a dose of a first medicament followed by a dose of a second medicament. Therefore, the disclosed dual-chamber drug delivery device may help to reduce the cost of manufacturing automatic injection devices.

It should be understood that the illustrated components are intended as an example only. In other example embodiments, fewer components, additional components, and/or alternative components are possible as well. Further, it should be understood that the above described and shown embodiments of the present disclosure are to be regarded as non-limiting examples and that they can be modified within the scope of the claims.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

I claim:

1. A drug delivery device comprising:
    a main exterior body;
    an interior body axially moveable with respect to the main exterior body;
    a dual-chamber reservoir arranged in the interior body and axially moveable with respect to the interior body, the dual-chamber reservoir comprising (i) a first chamber holding a first medicament, and (ii) a second chamber holding a second medicament;
    a first stopper slidably arranged in the dual-chamber reservoir;
    a second stopper slidably arranged in the dual-chamber reservoir, wherein the first chamber holding the first medicament is located between the first stopper and a proximal end of the dual-chamber reservoir, and wherein the second chamber holding the second medicament is located between the first stopper and the second stopper;
    a ruptureable membrane separating the first chamber from the second chamber;
    a needle in fluid communication with the dual-chamber reservoir, wherein the needle is directly coupled to the first stopper such that axial movement of the first stopper is directly transferred to the needle; and
    a plunger,
    wherein the axial movement of the interior body in a distal direction with respect to the main exterior body activates the drug delivery device, and
    wherein, after activation of the drug delivery device, the plunger is configured to (i) move the dual-chamber reservoir a given distance in a proximal direction with respect to the interior body so that a proximal end of the needle extends out of the interior body, and (ii) after moving the dual-chamber reservoir the given distance, move in the proximal direction with respect to the dual-chamber reservoir so as to eject from the needle the first medicament followed by the second medicament.

2. The drug delivery device of claim 1, further comprising a stopper grabber in contact with an inner surface of the dual-chamber reservoir, wherein the stopper grabber is configured to evenly distribute force from the plunger to the second stopper.

3. The drug delivery device of claim 1, wherein the ruptureable membrane is integrally formed as part of the first stopper.

4. The drug delivery device of claim 1, wherein the ruptureable membrane is configured to rupture due to a pressure imbalance between the first chamber and the second chamber that occurs when substantially all the first medicament in the first chamber is ejected.

5. The drug delivery device of claim 1, wherein, after the plunger moves the dual-chamber reservoir the given distance, (i) force from the plunger is transferred to the second stopper, (ii) the second stopper pushes the second medicament in the second chamber, (iii) the second medicament pushes the first stopper, and (iv) the first stopper pushes the first medicament in the first chamber out of the needle.

6. The drug delivery device of claim 1, further comprising:
    a collapsible needle cover covering the needle, wherein the collapsible needle cover is configured to collapse and be penetrated by the needle when the plunger moves the dual-chamber reservoir the given distance in the proximal direction with respect to the interior body so that the proximal end of the needle extends out of the interior body.

7. The drug delivery device of claim 1, wherein the dual-chamber reservoir is a dual-chamber syringe.

8. The drug delivery device of claim 1, further comprising a biasing member configured to bias the plunger in the proximal direction.

9. The drug delivery device of claim 8, wherein the biasing member is a spring.

10. A method comprising:
    in response to activation of the drug delivery device of claim 1, the plunger moving the dual-chamber reservoir through the interior body of the drug delivery device to force the needle out of the interior body, and to penetrate an injection site; and
    after moving the dual-chamber reservoir through the interior body of the drug delivery device to expose the needle and penetrate the injection site, the plunger moving through the dual-chamber reservoir to (i) force out of the drug delivery device substantially all the first medicament from the first chamber, (ii) subsequently rupture the ruptureable membrane to establish fluid communication between the needle and the second chamber, and (iii) subsequently force out of the drug delivery device substantially all of the second medicament from the second chamber.

11. The method of claim 10, the method further comprising:
  after being pressed against the injection site, the interior body, moving in the distal direction with respect to the main exterior body to activate the drug delivery device.

12. The method of claim 10, wherein the plunger moving through the dual-chamber reservoir to force out of the drug delivery device substantially all the first medicament followed by substantially all of the second medicament comprises:
  force from the plunger transferring to the second stopper;
  the second stopper pushing the second medicament in the second chamber;
  the second medicament pushing the first stopper;
  the first stopper pushing the first medicament in the first chamber out of the needle; and
  after the first stopper pushing the first medicament in the first chamber out of the needle, the second stopper pushing the second medicament in the second chamber out of the needle.

13. The drug delivery device of claim 1, wherein the ruptureable membrane is separately coupled to the first stopper.

\* \* \* \* \*